(12) United States Patent
Gao

(10) Patent No.: US 9,725,403 B2
(45) Date of Patent: *Aug. 8, 2017

(54) METHOD FOR PRETREATING AND USING COPPER-BASED CATALYST

(71) Applicant: Jiangsu Sinorgchem Technology Co., Ltd., Taizhou, Jiangsu Province (CN)

(72) Inventor: Shiming Gao, Shanghai (CN)

(73) Assignee: Jiangsu Sinorgchem Technology Co., Ltd., Taizhou, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/640,016

(22) Filed: Mar. 5, 2015

(65) Prior Publication Data

US 2015/0175523 A1  Jun. 25, 2015

Related U.S. Application Data

(63) Continuation of application No. 13/161,447, filed on Jun. 15, 2011, now Pat. No. 9,006,489.

(30) Foreign Application Priority Data

Jun. 7, 2011  (CN) .......................... 2011 1 0151516

(51) Int. Cl.
| | | |
|---|---|---|
| *C07C 209/24* | (2006.01) | |
| *B01J 37/08* | (2006.01) | |
| *B01J 37/18* | (2006.01) | |
| *B01J 23/72* | (2006.01) | |
| *B01J 23/80* | (2006.01) | |
| *B01J 23/83* | (2006.01) | |

(52) U.S. Cl.
CPC ............. *C07C 209/24* (2013.01); *B01J 23/72* (2013.01); *B01J 23/80* (2013.01); *B01J 23/83* (2013.01); *B01J 37/08* (2013.01); *B01J 37/18* (2013.01)

(58) Field of Classification Search
None
See application file for complete search history.

(56) References Cited

U.S. PATENT DOCUMENTS

| | | |
|---|---|---|
| 4,354,135 A | 10/1982 | Mitrofanov et al. |
| 4,435,279 A | 3/1984 | Busch et al. |
| 4,436,833 A | 3/1984 | Broecker et al. |
| 4,780,481 A | 10/1988 | Courty et al. |
| 4,791,141 A | 12/1988 | Chaumette et al. |
| 5,097,071 A | 3/1992 | Immel et al. |
| 5,481,048 A | 1/1996 | Tsukada et al. |
| 5,554,574 A | 9/1996 | Tsukada et al. |
| 5,591,873 A | 1/1997 | Bankmann et al. |
| 5,658,843 A | 8/1997 | Tsukada et al. |
| 5,817,872 A | 10/1998 | Honda et al. |
| 6,410,806 B2 | 6/2002 | Oku et al. |
| 6,787,496 B2 | 9/2004 | Daage et al. |
| 7,037,877 B1 | 5/2006 | Chaudhari et al. |
| 7,084,302 B2 | 8/2006 | Feng et al. |
| 7,405,327 B2 | 7/2008 | Haese et al. |
| 7,807,603 B2 | 10/2010 | Schlitter et al. |
| 8,450,530 B2 | 5/2013 | Mueller et al. |

FOREIGN PATENT DOCUMENTS

| | | |
|---|---|---|
| CN | 1617766 A | 5/2005 |
| CN | 101733169 A | 6/2010 |

OTHER PUBLICATIONS

Hong, Qingjun, Analysis of the Use of Copper-Based Catalystin in Synthesizing Antioxidant 4020, Jiangsu Chemical Industry, vol. 33(4), pp. 64, 65 and 70 (2005), China.
Li, Jun et al., Synthesis of p-Phenylenediam ine Derivatives as Antiaging Agents, Hecheng Huaxue, vol. 8(1), pp. 34-38 (2000), China (review article with English abstract).
Alfa Laval Product Article "Sour water stripping—crude oil refinery," pp. 1-3 (at least 2004).

*Primary Examiner* — Clinton Brooks
(74) *Attorney, Agent, or Firm* — Mei & Mark LLP; Manni Li

(57) ABSTRACT

Method for pretreating the copper-based catalyst having the steps of dehydrating the copper-based catalyst at an elevated temperature, reducing the dehydrated copper-based catalyst with hydrogen, and passivating the activated copper-based catalyst to obtain a catalyst suitable for N-alkylation. The dehydration and reduction steps may be conducted simultaneously.

15 Claims, No Drawings

METHOD FOR PRETREATING AND USING COPPER-BASED CATALYST

CROSS-REFERENCE TO RELATED APPLICATIONS

The subject application is a continuation of U.S. patent application Ser. No. 13/161,447 filed on Jun. 15, 2011, now allowed, which in turn claims priority on Chinese Patent Application No. 201110151516.2 filed on Jun. 7, 2011 in China. The contents and subject matter of the U.S. and Chinese priority applications are incorporated herein by reference.

TECHNICAL FIELD

The present invention relates to method for pretreating and using copper-based catalyst. The copper-based catalyst is particularly useful as a hydrogenation catalyst for the reductive alkylation for making p-phenylenediamine derivatives.

BACKGROUND OF THE INVENTION

The copper-based catalyst has been known to be used as a hydrogenation catalyst. For example, it has been used as the hydrogenation catalyst for making alcohols. For another example, it has been used for reductive alkylation for making p-phenylenediamine derivatives, including N-(1,3-dimethylbutyl)-N'-phenyl-p-phenylenediamine, N-isopropyl-N'-phenyl-p-phenylenediamine, and N-sec-octyl-N'-phenyl-p-phenylenediamine, which are rubber antidegradants. The derivatives are made by reacting 4-aminodiphenylamine with a ketone, which, depending on the desired derivative, may be acetone or methyl isobutyl ketone, etc., in the presence of hydrogen and the catalyst under suitable reaction conditions for N-alkylation. The copper-based catalyst is inexpensive and has been widely used for hydrogenation reactions.

Methods for making and activating the copper-based catalyst, mainly as the hydrogenation catalyst for making alcohols, are known. For examples, see U.S. Pat. Nos. 4,436,833; 4,780,481; 4,791,141; 5,591,873; 5,554,574; 5,481,048; 5,658,843; and 6,410,806. U.S. Pat. No. 7,807,603 relates to a catalyst extrudates based on copper oxide and their use for hydrogenating carbonyl compounds. U.S. Pat. No. 5,817,872 relates to a copper catalyst for the hydration of nitrile and the preparation thereof. U.S. Pat. No. 7,037,877 relates to a process for preparing copper chromite catalyst. U.S. Pat. No. 5,097,071 relates to a supported copper catalyst, process for preparing the catalyst, and process for preparing N-alkylated aromatic amines using the copper catalyst. In these patents, the copper-containing catalysts are treated or activated by an oxidizing or reducing reagent following the preparation steps. However, none of the patents address the problem encountered in using the copper-based catalyst as the hydrogenation catalyst for the N-alkylation for making the p-phenylenediamine derivatives.

When the active copper-based catalyst is used for the N-alkylation for making p-phenylenediamine derivatives, it exhibits poor selectivity and the reaction produces abundant side products and impurities. These side products and impurities mix with the final product and lower the quality of the product; they are difficult to separate and may cause the entire product batch to become waste and total loss of the catalyst.

SUMMARY OF THE INVENTION

The present invention provides a method for pretreating the copper-based catalyst which will result in a catalyst with high catalytic activity and selectivity suitable for the N-alkylation for making the antidegradants.

The method of the present invention has 3 main steps: first, dehydrating the copper-based catalyst at an elevated temperature; second, reducing the dehydrated copper-based catalyst with hydrogen; and third, passivating the activated copper-based catalyst to obtain a catalyst suitable for N-alkylation. The dehydration and reduction steps may be conducted simultaneously.

Further, the copper-based catalyst may be passivated by heating, reacting with 4-aminodiphenylamine made by the formanilide method and a ketone, or reacting with a sulfur or halogen-containing compound in the gas phase, a solution, or in a mixture with 4-aminodiphenylamine made by the nitrobenzene method and a ketone in the presence of hydrogen.

The present invention also provides a copper-based catalyst suitable for N-alkylation that is obtained through the pretreatment method.

The present invention further provides a method for making the alkylated derivatives of 4-aminodiphenylamine by reacting 4-aminodiphenylamine with a ketone in the presence of hydrogen and the passivated catalyst pretreated by the method of the present invention.

DETAILED DESCRIPTION OF THE INVENTION

In the present invention, the main component of the copper-based catalyst prior to the pretreatment is copper (II) oxide. The copper-based catalyst comprises about 10% to 70% copper oxide by weight, preferably about 30% to 50% copper oxide by weight, and more preferably about 38% to 42% copper oxide by weight. The copper-based catalyst may also have a carrier, which may be, for examples, ZnO, $Al_2O_3$, $SiO_2$, activated carbon, glass fiber net, ceramic ball, layered graphite, natural clay, cerium oxide, or a mixture thereof. Unlike copper (II) oxide, the carrier in the composition will not change its contents after the pretreatment. The content of ZnO in the catalyst may be more than 40% by weight. The content of $Al_2O_3$ may be more than 8% by weight.

The catalyst may be used in any form suitable for the reaction. For example, for a continuous reaction, the catalyst may be loaded to a column-shaped fixed bed to facilitate the reaction in a large volume. For another example, for a batchwise reaction, the catalyst may be loaded onto a reaction kettle-style bed. After the pretreatment according to the present invention, the catalyst shows high catalytic activity and selectivity for N-alkylation reduction reaction for making the alkylated derivatives of 4-aminodiphenylamine.

In the first step of the pretreatment method of the present invention, the copper-based catalyst is heated to an elevated temperature and water is removed from the composition. The dehydration step may be conducted in a sealed vessel that is filled with inert gas such as nitrogen gas. The pressure of the inert gas in the reactor is about 1 to 5 MPa and preferably about 2 MPa to 3 MPa. Under the protection of the ambient nitrogen gas, the temperature of the composition is gradually raised to more than about 100° C., preferably about 120° C. to 150° C., to remove water. The temperature is elevated at a rate of about 5° C. to 10° C. per hour during dehydration. The rate for raising the temperature may not be even. Preferably, the rate is faster when the temperature is lower, and the rate is accelerated when the temperature approaches the target temperature. The time for the dehydration step is about 4 to 12 hours, and preferably 6 to 10 hours. The dehydration step is concluded when the system temperature reaches the desirable temperature, i.e., more than about 100° C., and preferably about 120° C. to 150° C.

In the second step of the pretreatment, the copper-based catalyst is reacted with hydrogen for reduction and water produced during the reaction is removed from the composition. The step may be conducted in the liquid or gas phase, and hydrogen gas is fed into the reaction vessel at a volume concentration of about 0.1% to 100%, and preferably about 0.1% to 20%. Preferably, the step may be conducted under the protection of an inert gas such as nitrogen gas; it may also be conducted under pure hydrogen. The nitrogen gas acts as a carrier for the hydrogen gas and helps in preventing the overheating of the system such that the catalyst will be deactivated or the reaction vessel will be overheated by the heat generated in the hydrogenation reaction within a short period of time. The temperature of the reaction is about 110° C. to 280° C., preferably about 130° C. to 230° C. The reaction time is about 40 to 100 hours, preferably about 50 to 70 hours. After all the copper oxide (II) is reduced to metal copper, the hydrogenation step is complete.

During the hydrogenation reaction, it is important to control the temperature of the reaction and the rate for raising the temperature. Generally, the temperature is elevated at about 1° C. to 15° C. per hour, and preferably about 2° C. to 3° C. per hour. If the temperature is raised too quickly, the heat emitted from the reaction will accumulate and cause the inactivation of the catalyst and irreversibly damage to the reaction vessel. If the temperature is raised too slowly, the activation period is too long and it may be too difficult for the hydrogenation reaction to proceed and the oxide to be reduced completely.

The copper-based catalyst may be dehydrated and reduced simultaneously.

In the third step of the pretreatment, the activated copper-based catalyst is passivated to obtain a catalyst with proper catalytic activity and selectivity suitable for N-alkylation. At the conclusion of the hydrogenation step, copper oxide in the catalyst is reduced to copper metal with high activity. The activated copper-based catalyst has unstable activity and selectivity for N-alkylation reaction such as the reductive alkylation of 4-aminodiphenylamine and ketone in the presence of hydrogen to make derivatives. If the activated catalyst is used without being passivated, side reactions occur: the ketone is catalytically reduced to alcohol, the benzene ring is hydrogenated instead of the N-alkylation, and the long chain is broken. These side reactions greatly affect the selectivity for the N-alkylation reaction. Therefore, the catalyst must be passivated in order to have the requisite catalytic activity and selectivity suitable for the N-alkylation reaction for making the antidegradants.

In the first embodiment for passivating the activated catalyst of the present invention, the activated catalyst is passivated by heating or calcination at about 200° C. to 280° C., and preferably 240° C. to 260° C. The reaction time is about 1-80 hours, preferably about 1-5 hours, and more preferably about 2-3 hours. The pressure of an inert gas in the presence is about 0.1 MPa to 6 MPa. The crystalline copper will grow under the condition to become suitable for N-alkylation.

In the second embodiment for passivating the activated catalyst of the present invention, the activated catalyst is passivated by reacting with 4-aminodiphenylamine made by the formanilide method and a ketone in the presence of hydrogen gas. The reaction may be conducted continuously. The reaction temperature is about 100° C. to 180° C., and preferably about 120° C. to 150° C.; the pressure of the hydrogen gas is about 2 MPa to 6 MPa; the reaction time is about 20 to 40 hours. In the reaction mixture, the molar ratio of 4-aminodiphenylamine to ketone in the feed is about (1:1) to (1:4). As the reaction proceeds, the amount of 4-aminodiphenylamine decreases. When the concentration of 4-aminodiphenylamine is less than 1% by weight of the reaction mixture, the passivation step is complete, and the pretreated catalyst is ready for use for N-alkylation production.

4-Aminodiphenylamine made by the formanilide method is especially useful in the passivation of the catalyst due to their acquired properties during the production. The formanilide method is known in the art, for example, see U.S. Pat. No. 7,084,302. The method has the following reaction steps: first, formic acid reacts with aniline to form formanilide. Second, formanilide reacts with para-nitrochlorobenzene to form 4-nitrodiphenylamine. Third, 4-nitrodiphenylamine is reduced to 4-aminodiphenylamine. As para-nitrochlorobenzene is one of the starting materials for making 4-aminodiphenylamine in the reaction route, the final product of 4-aminodiphenylamine may contain residual chloride. During the reduction step, if sodium sulfide is used as the reduction agent, the final product of 4-aminodiphenylamine may also contain residual sulfide. Additionally, tars form during the refining process. All of the above residues and impurities in the 4-aminodiphenylamine made by the formanilide method make it suitable as the passivating agent for the activated copper-based catalyst in the present invention.

In the third embodiment for passivating the activated catalyst of the present invention, the activated catalyst is passivated by reacting with a sulfur or halogen-containing compound. The compound may be carbon disulfide, hydrogen sulfide, chlorophenylamine, 2-mercaptobenzothiazole, thiophene, or tetramethyl thiuram disulfide. The concentration of sulfur or halogen in the reaction mixture is about 1000 PPM to 10000 PPM, and preferably 4000 PPM to 6000 PPM. The passivation reaction is conducted in a gas phase, a solution, or in a mixture with 4-aminodiphenylamine made by the nitrobenzene method and a ketone in the presence of hydrogen gas. When the reaction is conducted in the gas phase, the sulfur or halogen-containing compound (usually has a low boiling point) is fed to the reaction system with a carrier, such as nitrogen gas, to passivate the copper-based catalyst. When the reaction is conducted in the solution, the sulfur or halogen-containing compound is first dissolved in an alcohol, ketone, or amine solvent, and then added to the catalyst for passivation.

The nitrobenzene method refers to the reaction route for making 4-aminodiphenylamine, in which aniline reacts with nitrobenzene to make the intermediates, i.e., 4-nitrodiphenylamine and 4-nitrosodiphenylamine, and then, the intermediates are hydrogenated to make 4-aminodiphenylamine under suitable reaction conditions and catalysts. The nitrobenzene method is known to the skilled in the art. For example, see U.S. Pat. No. 7,084,302. The reaction temperature is about 100° C. to 180° C., and preferably about 120° C. to 150° C.; the reaction time is about 20 to 40 hours; the pressure of the hydrogen gas is about 2 MPa to 8 MPa and preferably about 5 MPa to 7 MPa. In the reaction mixture, the molar ratio of 4-aminodiphenylamine to ketone is about (1:1) to (1:4).

The ratio of the halogen-containing compound to copper-based catalyst is about 0.05-1 mole halogen atom in the compound per kilogram of the catalyst prior to being treated. The sensitivity and effect of the passivating agent on the catalyst may vary and one of ordinary skill in the art should be able to determine the effect based on the present invention.

The copper-based catalyst pretreated by the method of the present invention comprises copper in the reduced metallic form and has high catalytic activity and selectivity for the N-alkylation reaction for making the p-phenylenediamine derivatives. The weight and appearance of the carrier remains the same as prior to the pretreatment. The yield of the derivatives is more than 99%, and the life of the catalyst is greatly extended, from about 3 months without the pretreatment of the present invention to about a year.

The catalyst is used for making the alkylated derivatives of 4-aminodiphenylamine by reacting 4-aminodiphenylamine with a ketone in the presence of hydrogen and the pretreated catalyst of the present invention. The reaction temperature is about 110° C. to 240° C., hydrogen pressure is about 2 MPa to 8 MPa and preferably about 5 MPa to 7 MPa. The reaction may be conducted batchwise or continuously. The total feed of 4-aminodiphenylamine and ketone is about 10 to 25% by weight per hour of the weight of the catalyst in a continuous reaction.

After the pretreatment process of the present invention, in a relatively short period of time, the copper catalyst achieves the desired reaction activity and selectivity. The waste product is greatly reduced. The passivation treatment of the copper-based catalyst eliminates the defective products in the early stage of the reductive alkylation reaction and shortens the time for the early stages of the production and the entire production time. Without the pretreatment of the present invention, the copper-based catalyst will not exhibit high catalytic activity and selectivity for N-alkylation.

The following examples further describe the present invention but do not limit the scope of the present invention. One of ordinary skill in the art will know how to make modifications based on the examples without departing from the scope of the present invention.

EXAMPLE 1

In a 100 ml continuous tabular reactor, a copper catalyst in the amount of 150 g is added. The copper catalyst contains 38.93% wt CuO, 40.84% wt ZnO, and 10.49% wt $Al_2O_3$. Nitrogen gas is fed into the reactor and eventually filled up the reactor with the pressure being maintained at 2.5 MPa. The nitrogen flow is controlled by the tail emission device to form a flow and maintain a proper gas to liquid ratio while facilitating the gas-liquid mass transfer.

The reactor is started to be heated, and the temperature increases at a velocity of about 10° C./hr. The copper catalysts starts to be dehydrated by heating. When the temperature approaches about 100° C., the velocity for the temperature increase is slowed down and the catalyst is kept at a temperature range of about 100-120° C. for 5 hours or so to completely remove the water from the copper catalyst.

When the temperature reaches about 120-125° C., a small amount of hydrogen gas is fed to the reactor. It is then observed that the temperature in the reactor rises from the heat emitted by the reaction. The feed amount or rate of the hydrogen gas is adjusted to avoid heating up the copper catalysts bed too quickly. Initially, the hydrogen gas flow is 1% by volume of the total gas flow. As the reductive hydrogenation of the copper-based catalyst proceeds, the volume percentage of the hydrogen gas is increased gradually. The reaction is being constantly observed, and once the concentration of the hydrogen gas flow remains the same in the feed and at the outlet, the reductive hydrogenation step has concluded and activated copper catalyst is obtained.

Next, the activated copper catalyst is passivated. A liquid mixture of 4-aminodiphenylamine made by the formanilide method and methyl isobutyl ketone (MIBK, also known as 4-methylpentan-2-one) is fed at a flow rate of 14 ml/hr into the reactor at a molar ratio of 1:1.8. The pressure of the hydrogen gas is adjusted to about 6 MPa; the reaction temperature is controlled at about 135-145° C. The weight percentage of 4-aminodiphenylamine is monitored. As the reaction proceeds, the product of the reaction, N-(1,3-Dimethylbutyl)-N'-phenyl-p-phenylenediamine, gradually increases as the peak value of the impurities decreases. After 12 hours of reaction, the weight percentage of the 4-aminodiphenylamine drops down to 0.8%, and the weight percentage of the product reaches 96.1%. It indicates that the pretreatment of the catalyst goes very well and the process is complete.

Now the copper-based catalyst is ready for production. While the feed of the liquid mixture of 4-aminodiphenylamine made from the formanilide method and MIBK is stopped, the reactor is still maintained at a hydrogen gas pressure of 6 MPa and a temperature of about 135-145° C. A liquid mixture of 4-aminodiphenylamine made by the nitrobenzene method and MIBK is fed at a molar ratio of 1:1.8. Once the reaction is complete, the final product, N-(1,3-Dimethylbutyl)-N'-phenyl-p-phenylenediamine is tested at the outlet. The weight percentage of 4-aminodiphenylamine in the inspected product is 0.3%, and the weight percentage of the product is 97.2%. As indicated in this example, the activity and selectivity of the pretreated copper catalyst quickly becomes stabilized for the alkylation reaction.

COMPARATIVE EXAMPLE 1

In a 100 ml continuous tabular reactor, a copper catalyst in the amount of 150 g with the same composition as the catalyst in Example 1 is added. Nitrogen gas is fed into the reactor and eventually filled up the reactor with the pressure being maintained at 2.5 MPa. The nitrogen flow is controlled by the tail emission device to form a flow and maintain a proper gas to liquid ratio while facilitating the gas-liquid mass transfer.

The reactor is started to be heated, and the temperature increases at a velocity of about 10° C./hr. The copper catalysts starts to be dehydrated by heating. When the temperature approaches about 100° C., the velocity for the temperature increase is slowed down and the catalyst is kept at a temperature range of about 100-120° C. for 5 hours or so to completely remove the water from the copper catalyst.

When the temperature reaches about 120-125° C., a small amount of hydrogen gas is fed to the reactor. It is then observed that the temperature in the reactor rises from the heat emitted by the reaction. The feed amount or rate of the hydrogen gas is adjusted to avoid heating up the copper catalysts bed too quickly. Initially, the hydrogen gas flow is 1% by volume of the total gas flow. As the reductive hydrogenation of the copper-based catalyst proceeds, the volume percentage of the hydrogen gas is increased gradually. The reaction is being constantly observed, and once the concentration of the hydrogen gas flow remains the same in the feed and at the outlet, the reductive hydrogenation step has concluded and activated copper catalyst is obtained.

Next, the activated copper catalyst is used without the passivation step. The reactor is maintained at a hydrogen gas pressure of 6 MPa and a temperature of about 135-145° C. A liquid mixture of 4-aminodiphenylamine made by the nitrobenzene method and MIBK is fed at a flow rate of 14 ml/hr and molar ratio of 1:1.8. Once the reaction is complete, the final product, N-(1,3-Dimethylbutyl)-N'-phenyl-p-phenylenediamine is tested at the outlet. The weight percentage of 4-aminodiphenylamine in the inspected product is 5.1% with many impurities. The reductive alkylation reaction is allowed to proceed for another 200 hours, however, the weight percentage of 4-aminodiphenylamine is still more than 1%. Thus, the 4-aminodiphenylamine can not be completely converted. As indicated in this comparative example, the activity and selectivity of the activated copper catalyst can not be quickly stabilized.

EXAMPLE 2

In a 100 ml continuous tabular reactor, a copper catalyst in the amount of 150 g having the same composition as Example 1 is added. Nitrogen gas is fed into the reactor and eventually filled up the reactor with the pressure being maintained at 2.5 MPa. The nitrogen flow is controlled by the tail emission device to form a flow and maintain a proper gas to liquid ratio while facilitating the gas-liquid mass transfer.

The reactor is started to be heated, and the temperature increases at a velocity of about 10° C./hr. The copper catalysts starts to be dehydrated by heating. When the temperature approaches about 100° C., the velocity for the temperature increase is slowed down and the catalyst is kept at a temperature range of about 100-120° C. for 5 hours or so to completely remove the water from the copper catalyst.

When the temperature reaches about 120-125° C., a small amount of hydrogen gas is fed to the reactor. It is then observed that the temperature in the reactor rises from the heat emitted by the reaction. The feed amount or rate of the hydrogen gas is adjusted to avoid heating up the copper catalysts bed too quickly. Initially, the hydrogen gas flow is 1% by volume of the total gas flow. As the reductive hydrogenation of the copper-based catalyst proceeds, the volume percentage of the hydrogen gas is increased gradually. The reaction is being constantly observed, and once the concentration of the hydrogen gas flow remains the same in the feed and at the outlet, the reductive hydrogenation step has concluded and activated copper catalyst is obtained.

Next, the activated copper-based catalyst is maintained at 230 to 235° C. for 12 hours to be passivated. Then, the pretreatment of the catalyst is complete.

Now the copper-based catalyst is ready for production. While the temperature of the reactor is lowered to 135-145° C., and the hydrogen gas pressure is adjusted to 6 MPa. A liquid mixture of 4-aminodiphenylamine made by the nitrobenzene method and MIBK is fed at a flow rate of 14 ml/hr and molar ratio of 1:1.8. As the reaction proceeds, the product, N-(1,3-Dimethylbutyl)-N'-phenyl-p-phenylenediamine, at the outlet is constantly monitored. Once it's confirmed that the amount of 4-aminodiphenylamine gradually decreases in the product, it shows that the reaction smoothly proceeds. The liquid mixture of the 4-aminodiphenylamine made by the nitrobenzene method and MIBK is continuously fed into the reactor and the reaction is allowed to proceed for 100 hours. Then, the product is examined. In the product, the weight percentage of 4-aminodiphenylamine is 0.8%, and the weight percentage of the product is 96.1%. As indicated in this example, the activity and selectivity of the pretreated copper catalyst quickly becomes stabilized for the alkylation reaction.

EXAMPLE 3

In a reactor for making the antidegradant, N-(1,3-Dimethylbutyl)-N'-phenyl-p-phenylenediamine, a copper catalyst having the same composition as Example 1 in the amount of 8 tons is loaded. After the reactor is tested for air-tightness and pressure, nitrogen gas is fed into the reactor and eventually filled up the reactor with the pressure being maintained at 2.5 MPa. The air circulator is started. Then, the reactor is started to be heated, and the temperature increases at a velocity of about 10-15° C./hr. When the temperature reaches 110° C., the catalyst is maintained at that temperature for 4-6 hours to completely remove the water from the copper catalyst.

Then, hydrogen gas is fed to the reactor. It is then observed that the temperature in the reactor rises from the heat emitted by the reaction. The temperature of the copper catalyst bed is controlled and monitored as well as the pressure and temperature of the system. The overheating of the catalyst bed caused by the heat emitted from the hydrogenation reaction should be avoided. Initially, the hydrogen gas flow is 0.5% by volume of the total gas flow. As the reductive hydrogenation of the copper-based catalyst proceeds, the volume percentage of the hydrogen gas is increased gradually. The reaction is being constantly observed, and once the concentration of the hydrogen gas flow remains the same in the feed and at the outlet, the reductive hydrogenation step has concluded and activated copper catalyst is obtained. Alternatively, the count on the meter for the hydrogen gas through the inlet into the reactor is recorded and the actual amount of hydrogen gas that enters the reactor is calculated in comparison with the theoretical amount of hydrogen gas that needs to be consumed in order to hydrogenate the fed copper oxide. When the actually consumed hydrogen gas is about the same as the theoretical value of the hydrogen consumption, coupled with the fact that the concentration of the hydrogen gas before and after flowing through the catalyst bed remains the same, then, it is confirmed that the hydrogenation activation is complete and the activated catalyst goes into the next step of passivation.

Next, the temperature of the reactor is lowered to 135-145° C., and a liquid mixture of 2,4-dichloroaniline dissolved in isopropanol is fed into the reactor at a flow rate of 1000 L/hr. The amount of chlorine in the liquid mixture is 3000 PPM. The passivation step is complete after 24 hours of treatment.

Then, the copper-based catalyst is ready for production. The reactor is adjusted to have a hydrogen gas pressure of about 6 MPa. A liquid mixture of 4-aminodiphenylamine made by the nitrobenzene method and MIBK is fed at a molar ratio of 1:1.8 to make the final product, N-(1,3-Dimethylbutyl)-N'-phenyl-p-phenylenediamine. The final product is tested at the outlet. The weight percentage of 4-aminodiphenylamine in the product is 0.5%, and the weight percentage of the product is 97.6%. As indicated in this example, the activity and selectivity of the pretreated copper catalyst quickly becomes stabilized for the alkylation reaction.

EXAMPLE 4

In a high pressure stainless steel tabular reactor having a length of 1500 mm, ceramic balls and filter net are installed at both ends along with a copper catalyst in the amount of 1500 g, which contains 39.15% wt CuO, 40.12% wt ZnO, and 10.5% wt $Al_2O_3$. After the installation of the catalyst, the system is tested for air-tightness by nitrogen gas feed. Then, nitrogen gas is fed into the reactor for air exchange and eventually filled up the reactor at a flow rate of 380 L/hr. The nitrogen flow is controlled to ensure the timely removal of heat during the reduction stage and the gas-liquid ratio.

The reactor is started to be heated, and the temperature increases at a velocity of about 10° C./hr before the temperature reaches 80° C., and the velocity for the temperature increase is decreased to 5° C./hr once the temperature goes above 80° C. The copper catalyst is dehydrated by heating. When the temperature reaches 120° C., hydrogen gas is fed into the reactor intermittently to start the hydrogenation reaction while water is continuously being removed from the reactor.

After the hydrogen gas is fed to the reactor intermittently for 30 minutes, it is continuously fed into the reactor at gradually increased concentration of 0.2%, while the temperature of the catalyst bed is increased at 2-3° C./hr and water is removed from the system. Once the temperature reaches 230° C. and the calculated amount of water produced in the hydrogenation reaction is the same as the water actually removed from the reactor, while the concentration of the hydrogen gas flow remains the same in the feed and at the outlet, the reductive hydrogenation step has concluded and activated copper catalyst is obtained.

Then, the reactor is maintained at 230-240° C. for 2 hours and the temperature starts to decrease until it reaches 130° C. Nitrogen gas in the system is exchanged with hydrogen gas to have a pressure at 6.0 MPa, and the catalyst is to be passivated. A liquid mixture containing para-chlorophenylamine dissolved in MIBK is fed into the reactor at a flow rate of 140 L/hr. The amount of chlorine in the MIBK solvent is 2000 PPM, and the total amount of the liquid mixture is about 9 L. The passivation treatment lasts for 64 hours.

Then, a liquid mixture of 4-aminodiphenylamine and MIBK is fed to the reactor at a volume ratio of 1:(1.3-1.4). The reactor is maintained at a hydrogen pressure of 6.0 MPa and temperature of 135-140° C. The total feed of MIBK and 4-aminodiphenylamine is 140 L/hour. The product, N-(1,3-Dimethylbutyl)-N'-phenyl-p-phenylenediamine, is tested at the outlet. The weight percentage of 4-aminodiphenylamine in the inspected product is 0.6%, and the weight percentage of the product is more than 96%. As indicated in this example, the activity and selectivity of the pretreated copper catalyst is stabilized for the reaction.

I claim:

1. A method for pretreating a copper-based catalyst comprising
   dehydrating a copper-based catalyst at an elevated temperature,
   reducing the dehydrated copper-based catalyst with hydrogen to obtain an activated copper-based catalyst, and
   passivating the activated copper-based catalyst to obtain a catalyst suitable for N-alkylation by reacting with a sulfur- or halogen-containing compound,
   wherein the copper-based catalyst comprises about 10% to 70% copper oxide; and
   concentration of the sulfur- or halogen-containing compound is about 1000 PPM to 10000 PPM for passivation; and
   the sulfur- or halogen-containing compound is selected from the group consisting of carbon disulfide, chlorophenylamine, 2-mercaptobenzothiazole, thiophene, 2,4-dichloroaniline, and tetramethyl thiuram disulfide.

2. The method of claim 1, wherein the copper-based catalyst further comprises a carrier that is ZnO, $Al_2O_3$, $SiO_2$, activated carbon, glass fiber net, ceramic ball, layered graphite, natural clay, cerium oxide, or a mixture thereof, and the carrier does not change its contents after the catalyst being pretreated.

3. The method of claim 1, wherein the copper-based catalyst is dehydrated at the elevated temperature of more than about 100° C. and under pressure of an inert gas at about 1 MPa to 5 MPa.

4. The method of claim 1, wherein the temperature is elevated at about 5° C. to 10° C. per hour during dehydration.

5. The method of claim 1, wherein the dehydrated copper-based catalyst is reduced with hydrogen in a liquid phase or a gas phase.

6. The method of claim 1, wherein the dehydrated copper-based catalyst is reduced at a temperature of about 110° C. to 280° C. and the hydrogen gas is fed at a volume concentration of about 0.1% to 100%.

7. The method of claim 1, wherein the temperature for reduction is elevated at about 1° C. to 15° C. per hour.

8. The method of claim 1, wherein the copper-based catalyst is dehydrated and reduced simultaneously.

9. The method of claim 1, wherein a ratio of the sulfur- or halogen-containing compound to the copper-based catalyst is about 0.05-1 mole per kilogram catalyst.

10. The method of claim 1, wherein the copper-based catalyst is passivated in a gas phase, and the sulfur- or halogen-containing compound is fed to the reaction with a carrier.

11. The method of claim 1, wherein the copper-based catalyst is passivated in a solution, and the sulfur- or halogen-containing compound is dissolved in an alcohol, ketone, or an amine solvent to form the solution for passivating the catalyst.

12. The copper-based catalyst pretreated by the method of claim 1.

13. The method for making alkylated derivatives of 4-aminodiphenylamine according to claim 1, comprising
   reacting 4-aminodiphenylamine with a ketone in presence of hydrogen and the copper-based catalyst pretreated by the method of claim 1.

14. The method of claim 13, wherein the reaction is conducted at a temperature of about 110° C. to 240° C. under a hydrogen pressure of about 2 MPa to 8 MPa.

15. The method of claim 13, wherein the reaction is conducted continuously, and a total feed amount of 4-aminodiphenylamine and ketone is about 10 to 25% by weight per hour of the weight of the catalyst.

* * * * *